US012708323B2

(12) United States Patent
Choi et al.

(10) Patent No.: US 12,708,323 B2
(45) Date of Patent: Aug. 18, 2026

(54) DEVICE FOR PROVIDING INFORMATION FOR IMPROVING SLEEP QUALITY AND METHOD THEREOF

(71) Applicant: SAMSUNG ELECTRONICS CO., LTD., Suwon-si (KR)

(72) Inventors: Minseok Choi, Suwon-si (KR); Jaehwan Lee, Suwon-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 416 days.

(21) Appl. No.: 18/244,064

(22) Filed: Sep. 8, 2023

(65) Prior Publication Data

US 2023/0414171 A1 Dec. 28, 2023

Related U.S. Application Data

(63) Continuation of application No. PCT/KR2022/001027, filed on Jan. 20, 2022.

(30) Foreign Application Priority Data

Mar. 9, 2021 (KR) ........................ 10-2021-0030968

(51) Int. Cl.
*A61B 5/00* (2006.01)
*A61B 5/11* (2006.01)
(Continued)

(52) U.S. Cl.
CPC ................ *A61B 5/486* (2013.01); *A61B 5/11* (2013.01); *A61B 5/4809* (2013.01);
(Continued)

(58) Field of Classification Search
CPC ......... A61B 5/486; A61B 5/11; A61B 5/4809; A61B 5/4815; A61B 5/681; A61B 5/742;
(Continued)

(56) References Cited

U.S. PATENT DOCUMENTS

| | | | |
|---|---|---|---|
| 10,555,698 | B2 | 2/2020 | Russell et al. |
| 2011/0218454 | A1 | 9/2011 | Low |

(Continued)

FOREIGN PATENT DOCUMENTS

| | | | |
|---|---|---|---|
| CN | 110491468 | A | 11/2019 |
| JP | 2016187429 | A | 11/2016 |

(Continued)

OTHER PUBLICATIONS

International Search Report with Written Opinion for International Application No. PCT/KR2022/001027; International Filing Date Jan. 20, 2022; Date of Mailing May 16, 2022; 62 Pages.

(Continued)

*Primary Examiner* — An T Nguyen
(74) *Attorney, Agent, or Firm* — CANTOR COLBURN LLP

(57) ABSTRACT

A method for providing information for improving sleep quality, and an electronic device for supporting same are disclosed. The electronic device may comprise a display, at least one processor, and a memory. The at least one processor may: check a user's sleep time information, obtain activity information and sleep evaluation information corresponding to the sleep time information; analyze a pattern of the activity information on the basis of the sleep evaluation information; generate sleep guide information relating to the user on the basis of a result of the analysis; and output the generated sleep guide information on the display. Various other embodiments identified by the present document are possible.

13 Claims, 20 Drawing Sheets

(51) Int. Cl.
*G16H 10/60* (2018.01)
*G16H 20/70* (2018.01)

(52) U.S. Cl.
CPC ........... *A61B 5/4815* (2013.01); *G16H 10/60* (2018.01); *G16H 20/70* (2018.01); *A61B 5/681* (2013.01); *A61B 5/742* (2013.01); *A61B 2562/0219* (2013.01)

(58) Field of Classification Search
CPC . A61B 2562/0219; A61B 5/0077; A61B 5/01; A61B 5/02405; A61B 5/02416; A61B 5/02438; A61B 5/1118; A61B 5/1123; A61B 5/318; A61B 5/7267; A61B 5/4812; A61B 5/1116; A61B 5/7264; A61B 5/7465; G16H 10/60; G16H 20/70; G16H 40/63; A61M 21/02
See application file for complete search history.

(56) References Cited

U.S. PATENT DOCUMENTS

| | | | |
|---|---|---|---|
| 2011/0230790 A1 | 9/2011 | Kozlov | |
| 2013/0018284 A1 | 1/2013 | Kahn et al. | |
| 2014/0088378 A1 | 3/2014 | Muzet | |
| 2015/0367097 A1 | 12/2015 | Gavish | |
| 2017/0173299 A1 | 6/2017 | Lee et al. | |
| 2019/0069839 A1 | 3/2019 | Park et al. | |
| 2020/0009349 A1 | 1/2020 | Shouldice et al. | |
| 2020/0027552 A1 | 1/2020 | Lee | |
| 2020/0111569 A1 | 4/2020 | Lim et al. | |
| 2020/0146619 A1 | 5/2020 | Molina et al. | |
| 2020/0237295 A1 | 7/2020 | Lee et al. | |
| 2021/0361179 A1 | 11/2021 | Lee et al. | |
| 2022/0005580 A1* | 1/2022 | Pavlov | A61B 5/486 |
| 2023/0148956 A1* | 5/2023 | Narayanan | A61B 5/4809 600/301 |

FOREIGN PATENT DOCUMENTS

| | | | |
|---|---|---|---|
| JP | 2018026006 A | 2/2018 |
| JP | 6414940 B2 | 10/2018 |
| JP | 6698521 B2 | 5/2020 |
| JP | 2020526320 A | 8/2020 |
| KR | 1020110094064 | 8/2011 |
| KR | 1020170028247 | 3/2017 |
| KR | 20170074364 A | 6/2017 |
| KR | 1020170074000 | 6/2017 |
| KR | 101964733 B1 | 4/2019 |
| KR | 1020190095820 | 8/2019 |
| KR | 1020190104484 | 9/2019 |
| KR | 102090968 B1 | 3/2020 |
| KR | 102143499 B1 | 8/2020 |
| KR | 1020200094344 | 8/2020 |

OTHER PUBLICATIONS

Korean Office Action Issued In KR Application No. 10-2021-0030968; Mail Date Feb. 11, 2026; 13 Pages.

* cited by examiner

600

| name | type | value |
|---|---|---|
| Action Type (601) | Object | classification of action |
| Action Name (603) | string | action name |
| Occurrence Type (605) | int | whether action occurs at bedtime/wake-up time |
| Occurrence Gap (607) | long | occurrence gap between action and bedtime/wake-up time |
| Start Time (609) | long | Action start time |
| End Time (611) | long | Action end time |
| Time Offset (613) | long | Time Offset |

FIG.6

DEVICE FOR PROVIDING INFORMATION FOR IMPROVING SLEEP QUALITY AND METHOD THEREOF

CROSS-REFERENCE TO RELATED APPLICATIONS

This application is a continuation application, claiming priority under § 365(c), of International Application No. PCT/KR2022/001027, filed on Jan. 20, 2022, which is based on and claims the benefit of Korean patent application number 10-2021-0030968 filed on Mar. 9, 2021, in the Korean Intellectual Property Office, the disclosures of which are incorporated by reference herein in their entireties.

TECHNICAL FIELD

Various embodiments of the disclosure relate to a technology for providing information for improving the sleep quality of a user through an electronic device.

BACKGROUND ART

As the use of mobile electronic devices has become more common due to the recent development of mobile communication technology, services or functions provided through the mobile electronic devices are gradually diversifying. For example, a healthcare service for continuously monitoring a user's biometric information through the mobile electronic device and managing health may be provided.

The mobile electronic device may acquire biometric data of the user from one or more sensors or a wearable device (for example, a smart watch) which can be linked to the mobile electronic device and analyze a health condition of the user on the basis of the acquired biometric signal. The mobile electronic device may allow the user to maintain a healthy body by providing information on an exercise state during an activity time of the user or a sleep state during a sleep time of the user.

DISCLOSURE OF INVENTION

Technical Problem

As the interest in health increases, providing information on a sleep activity accounting for about 25% of the day has become an important function. A current mobile electronic device may analyze sleep states of a user on the basis of biometric data collected through a link with one or more sensors included in the electronic device or a wearable device and provide the analysis result to the user. For example, the electronic device may analyze sleep levels, such as awakening during sleep, light non-rapid-eye-movement (REM) sleep, deep non-REM sleep, or REM sleep, on the basis of biometric data collected while the user sleeps, score the analyzed sleep level, and provide the same to the user. However, current mobile electronic devices simply provide the sleep analysis result and have limitations in providing practical feedback to improve a sleep state of the user.

Solution to Problem

Accordingly, one or more embodiments of the disclosure continuously analyze and manage the sleep habit of the user by collecting action information of the user which may influence sleep and sleep evaluation information and analyzing a pattern of action information on the basis of the sleep evaluation information. Further, various embodiments for providing actual sleep guide information that helps for improving the sleep state of the user on the basis of the analyzed sleep habit of the user may be provided.

The technical subject matter pursued in embodiments of the disclosure may not be limited to the above mentioned technical subject matter, and other technical matter which are not mentioned may be clearly understood, through the following descriptions, by those skilled in the art of the disclosure.

An electronic device according to an embodiment of the disclosure includes a display, at least one processor operatively connected to the display, and a memory operatively connected to the at least one processor, wherein the memory is configured to store instructions causing the at least one processor to, when executed, identify sleep time information of a user, acquire sleep evaluation information and action information corresponding to the sleep time information, analyze a pattern of the action information, based on the sleep evaluation information, generate sleep guide information for the user, based on a result of the analysis, and output the generated sleep guide information to the display.

A method of operating an electronic device according to one or more embodiments of the disclosure includes identifying sleep time information of a user, acquiring sleep evaluation information and action information corresponding to the sleep time information, analyzing a pattern of the action information, based on the sleep evaluation information, generating sleep guide information for the user, based on a result of the analysis, and outputting the generated sleep guide information to the display.

Advantageous Effects of Invention

Various embodiments of the disclosure can analyze an action pattern which may influence the sleep quality of the user to provide feedback corresponding to a sleep habit of the user. Further, one or more embodiments can provide information on the correlation between the sleep quality and the sleep habit to the user on the basis of statistical data on the sleep habit of the user and provide a detailed guide for improving the sleep quality.

In addition, various effects directly or indirectly detected through the disclosure can be provided.

BRIEF DESCRIPTION OF DRAWINGS

FIG. 6 illustrates a scheme of collecting and managing action information according to an embodiment.

In connection with description of drawings, the same or similar reference numerals may be used for the same or similar elements.

MODE FOR CARRYING OUT THE INVENTION

Hereinafter, various embodiments of the disclosure are described with reference to the accompanying drawings. However, this does not limit various embodiments of the disclosure to the specific form, and it should be understood that various modifications, equivalent, and/or alternative of the disclosure are included.

Figure 1:
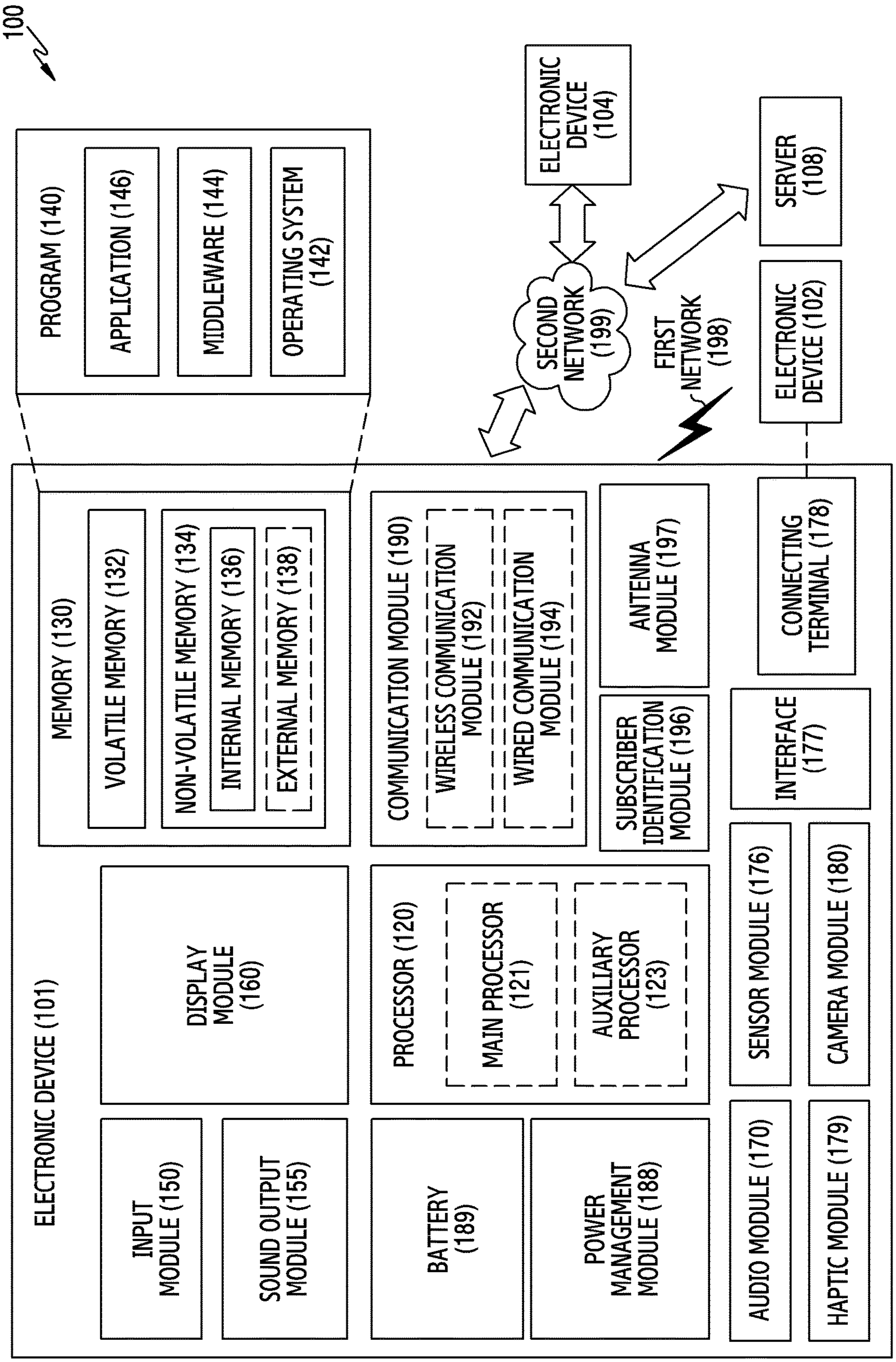
FIG. 1 is a block diagram illustrating an electronic device within a network environment according to an embodiment.

FIG. 1 is a block diagram illustrating an electronic device 101 in a network environment 100 according to various embodiments.

Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments, at least one of the components (e.g., the connecting terminal 178) may be omitted from the electronic device 101, or one or more other components may be added in the electronic device 101. In some embodiments, some of the components (e.g., the sensor module 176, the camera module 180, or the antenna module 197) may be implemented as a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thererto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by other component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving calls. According to an embodiment, the receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. According to an embodiment, the display module 160 may include a touch sensor adapted to detect a touch, or a pressure sensor adapted to measure the intensity of force incurred by the touch.

The audio module 170 may convert a sound into an electrical signal and vice versa. According to an embodiment, the audio module 170 may obtain the sound via the input module 150, or output the sound via the sound output module 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a 5G network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., a printed circuit board (PCB)). According to an embodiment, the antenna module 197 may include a plurality of antennas (e.g., array antennas). In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

According to various embodiments, the antenna module 197 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 or 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In another embodiment, the external electronic device 104 may include an internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or healthcare) based on 5G communication technology or IoT-related technology.

Figure 2:
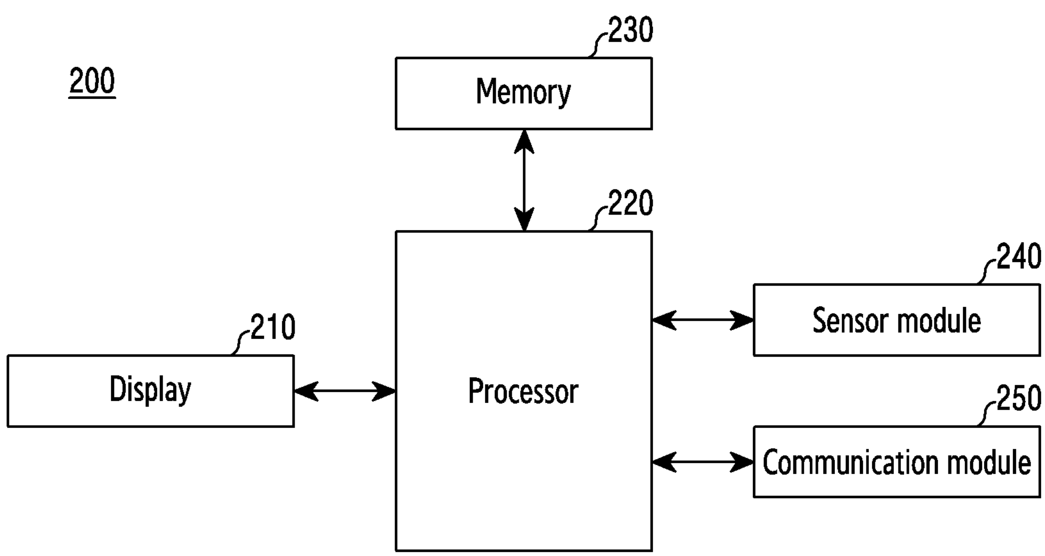
FIG. 2 is a block diagram illustrating a configuration of the electronic device according to an embodiment.

FIG. 2 is a block diagram illustrating a configuration of an electronic device 200 according to an embodiment.

Referring to FIG. 2, the electronic device 200 is a device which measures and analyzes a sleep state of a user to assist the user in having good sleep habits and improving bad sleep habits, and may include a display 210, a processor 220, a memory 230, a sensor module 240, or a communication module 250. In FIG. 2, the electronic device 200 may correspond to the electronic device 101 and may include one or more software and hardware components of the electronic device 101 illustrated in FIG. 1.

In an embodiment, the display 210 (for example, the display module 160 of FIG. 1) may display the measured sleep state of the user and sleep guide information corresponding to the sleep state. According to various embodiments, the display 210 may output a user interface for acquiring user sleep time information or user sleep evaluation information.

In an embodiment, the display module 210 may be configured by at least one of a liquid crystal display (LCD), a thin film transistor LCD (TFT-LCD), an organic light emitting diode (OLED), LED, active matrix OLED (AMOLED), a flexible display, and a three-dimensional display. Further, some of the displays may be configured to be transparent or be a light-transmitting type so that the outside can be seen therethrough. The display may be implemented in a transparent display type including transparent OLED (TOLED).

In an embodiment, the memory 230 (for example, the memory 130 of FIG. 1) may store instructions which control at least one processor 220 (for example, the processor 120 of FIG. 1) to perform various operations. For example, at least one processor 220 may perform operations for analyzing the user sleep habit on the basis of sleep-related information collected for the user and providing information for improving the user sleep quality by using the analysis result.

In an embodiment, the memory 230 may store sleep-related information (for example, user movement information and/or biometric data), sleep state information, sleep evaluation information, and/or predetermined condition information acquired through an external electronic device (for example, a smart watch, a smart band, or a smart ring) or the sensor module 240.

In an embodiment, at least one processor 220 may identify user sleep time information. The sleep time information is an index indicating how much time the user sleeps during one day and may be calculated on the basis of bedtime and wake-up time of the user. According to various embodiments, at least one processor 220 may identify the sleep time information on the basis of at least one of a user input, a screen on or screen off record of the electronic device, and/or user biometric data. For example, at least one processor 220 may receive an input of the bedtime and the wake-up time from the user or may estimate the bedtime and the wake-up time of the user on the basis of the screen on or screen off record detected by the display 210. In another example, at least one processor 220 may estimate the bedtime and the wake-up time of the user on the basis of the user biometric information acquired from the sensor module 240 or an external electronic device (for example, a smart watch, a smart band, or a smart ring) linked to the electronic device 200.

In an embodiment, at least one processor 220 may acquire sleep evaluation information corresponding to the sleep time information. The sleep evaluation information is an index that reflects evaluation for the (user) sleep and may be determined on the basis of one or more evaluation items. For example, at least one processor 220 may acquire the sleep evaluation information on the basis of at least one evaluation item among a sleep score calculated on the basis of the sleep state recorded during the sleep, sleep satisfaction input by the user, sleep efficiency indicating a ratio of the actual sleep time to the total sleep time, and/or a sleep rating determined on the basis of the sleep time information. The sleep score is an item for objectively evaluating the sleep quality in consideration of one or more evaluation reference elements and may be scoring of the sleep quality within a range from, for example, 0 to 100 on the basis of the one or more evaluation reference elements determined by the American sleep foundation. For example, the evaluation reference elements may reflect sleep states such as sleep time, sleep cycle, sleep level, and/or movement during sleep. At least one processor 220 may analyze a change in sleep levels or a sleep cycle on the basis of biometric data (for example, heart rate (HR) or heart rate variability (HRV)) detected during the sleep time of the user and a degree of motion during sleep and calculate a sleep score corresponding to the analysis result. For example, the biometric data detected by at least one processor 220 during the sleep time of the user may include electrocardiogram information and/or various biometric signals for detecting the sleep states of the user as well as the heart rate or the heart rate variability. The sleep levels may be divided into awakening, light non-REM sleep, deep non-REM sleep, and/or REM sleep, and the sleep cycle may be determined according to the change in the sleep level. The sleep satisfaction is an item that reflects a user's subjective evaluation on sleep and may be determined by a user input. The sleep efficiency is an item indicating the actual sleep time except for the time in which user movement exceeds a predetermined level in the total sleep time and may be defined as a range from 0 to 100%. The sleep rating may be an item evaluated on the basis of at least one of a bedtime, a wake-up time, or waking hours during sleep. According to various embodiments, at least one processor 220 may collect sleep evaluation items including at least one of the sleep score, the sleep satisfaction, the sleep efficiency, and/or the sleep rating and may store and/or manage the same in the memory 230 or a database which can be accessed by the electronic device 200.

In an embodiment, at least one processor 220 may acquire action information corresponding to the sleep time information. The action information is an index indicating a user's action which may influence sleep and may be determined in consideration of motion of the user or data collected through the electronic device 200. For example, at least one processor 220 may acquire the action information on the basis of at least one of a usage record of an application executed by the electronic device 200, a record related to motion of the user detected by the sensor module 240 or an external electronic device (for example, a smart watch), and/or context data estimated on the basis of a network connection state of the electronic device 200. The usage record of the application may be acquired on the basis of log data recorded in connection with an application executed by the user, and the motion-related record may be acquired on the basis of at least one of a recorded step count of the user, quantity of motion, heartbeat data, and/or whether the user takes a nap. The context data indicates data related to the action or environment of the user estimated through the electronic device 200 and may be acquired on the basis of at least one of a phone call log of the user, location information, and/or weather information. According to various embodiments, the action information may be stored and managed in a predetermined format to analyze the user's sleep habit. At least one processor 220 may convert the action information into a first format including at least one of an action type, an action name, a time difference between an action occurrence time point and sleep time, an action start time, and/or an action end time and store and/or manage the action information converted into the first format in the memory 230 or a database which can be accessed by the electronic device 200. For example, when acquiring action information indicating the use of a game application for one hour before the user goes to bed, at least one processor 220 may convert and manage the acquired action information according to the first format. In another example, at least one processor 220 may not consider an exercise record generated in a time zone irrelevant to the sleep time of the user (for example, the time difference between the action occurrence time point and the sleep time is larger than or equal to a predetermined time difference) as the action information that influences the sleep states of the user.

In an embodiment, at least one processor 220 may analyze a pattern of the action information on the basis of the acquired sleep evaluation information. When it is identified that the sleep evaluation information collected according to first sleep time information satisfies a predetermined reference, at least one processor 220 may classify the action information collected according to the sleep time information as a positive pattern. The predetermined reference may be determined on the basis of at least one evaluation item included in the sleep evaluation information. For example, when it is identified that the sleep score corresponding to the first sleep time information is larger than an average sleep score of the user's age, at least one processor 220 may classify action information collected according to the first sleep time information as a positive pattern. On the other hand, when it is identified that the sleep evaluation collected according to second sleep time information does not satisfy the predetermined reference, at least one processor 220 may classify action information corresponding to the second sleep time information as a negative pattern. For example, when it is identified that the sleep efficiency corresponding to the second sleep time information is lower than a predetermined reference (for example, 80%), at least one processor 220 may classify action information collected according to the second sleep time information as a negative pattern. At least one processor 220 may store the classification result in the memory 230 or a database which can be accessed by the electronic device 200 to manage the same. According to various embodiments, at least one processor 220 may transmit the collected action information to an external server (for example, the server 108 of FIG. 1) and receive the analyzed result from the external server. For example, the external server may analyze which action information influences the user's sleep quality on the basis of a deep learning algorithm and transmit the analysis result to the electronic device 200.

In an embodiment, at least one processor 220 may determine a user's sleep habit on the basis of the classification result of the action information. For example, at least one processor 220 may determine a positive pattern having the highest frequency in the memory 230 or the database as a first sleep habit of the user. At least one processor 220 may determine a negative pattern having the highest frequency in the memory 230 or the database as a second sleep habit of the user.

In an embodiment, at least one processor 220 may generate sleep guide information of the user on the basis of the pattern analysis result of the action information. For example, at least one processor 220 may generate the sleep guide information on the basis of at least one of the first sleep habit or the second sleep habit. The sleep guide information may be generated to include the content that helps for continuously maintaining the first sleep habit belonging to the positive pattern or the content that helps for improving the second sleep habit belonging to the negative pattern. According to various embodiments, at least one processor 220 may generate the sleep guide information in consideration of a profile of the user. The profile may include at least one of gender, age, and/or residence of the corresponding user. For example, when the user is a male in his thirties (30s), at least one processor 220 may generate sleep statistics for men in their 30s and a comment for improving the sleep quality as the sleep guide information.

In an embodiment, at least one processor 220 may output the generated sleep guide information. When a predetermined condition (for example, time or location) is satisfied, at least one processor 220 may output the sleep guide information through the display 210 and/or at least one of the output means (for example, the first sound output module 155 and the haptic module 179) included in the electronic device 200. The output condition of the sleep guide information may be preset by the user. For example, when the time configured as the sleep guide information output time by the user arrives, at least one processor 220 may perform control to output the sleep guide information on the display 210.

In an embodiment, the sensor module 240 (for example, the sensor module 176 of FIG. 1) may be used to acquire the sleep time information and/or the action information. For example, the sensor module 240 may detect the user's sleep state by using at least one of a heartbeat sensor (for example, a photoplethysmography (PPG) sensor), an electrocardiogram (for example, an electrocardiogram (ECG) sensor), an acceleration sensor, and/or a gyro sensor, and at least one processor 220 may acquire the sleep time information on the basis of a time interval in which the sleep state detected by the sensor module 240 is maintained. In another example, the sensor module 240 may detect the user's motion by using at least one of the acceleration sensor or the gyro sensor, and at least one processor 220 may acquire the action information on the basis of motion-related data detected by the sensor module 240. In addition, the sensor module 240 may include various sensors capable of acquiring the sleep state of the user and/or the action information of the user.

In an embodiment, the sensor module 240 may further include at least one sensor (for example, a temperature sensor, a humidity sensor, an illumination sensor, a camera sensor, a gas sensor, and/or a fine dust sensor) for acquiring context data related to an environment of the user.

In an embodiment, the communication module 250 (for example, the communication module 190 of FIG. 1) may configure a communication connection with an external electronic device and transmit sleep-related data to the external electronic device or receive the same from the external electronic device. According to various embodiments, the communication module 250 may support at least one communication scheme among cellular communication, wireless fidelity (Wi-Fi), Bluetooth, near field communication (NFC), or ultra-wide band (UWB) communication.

Figure 3:
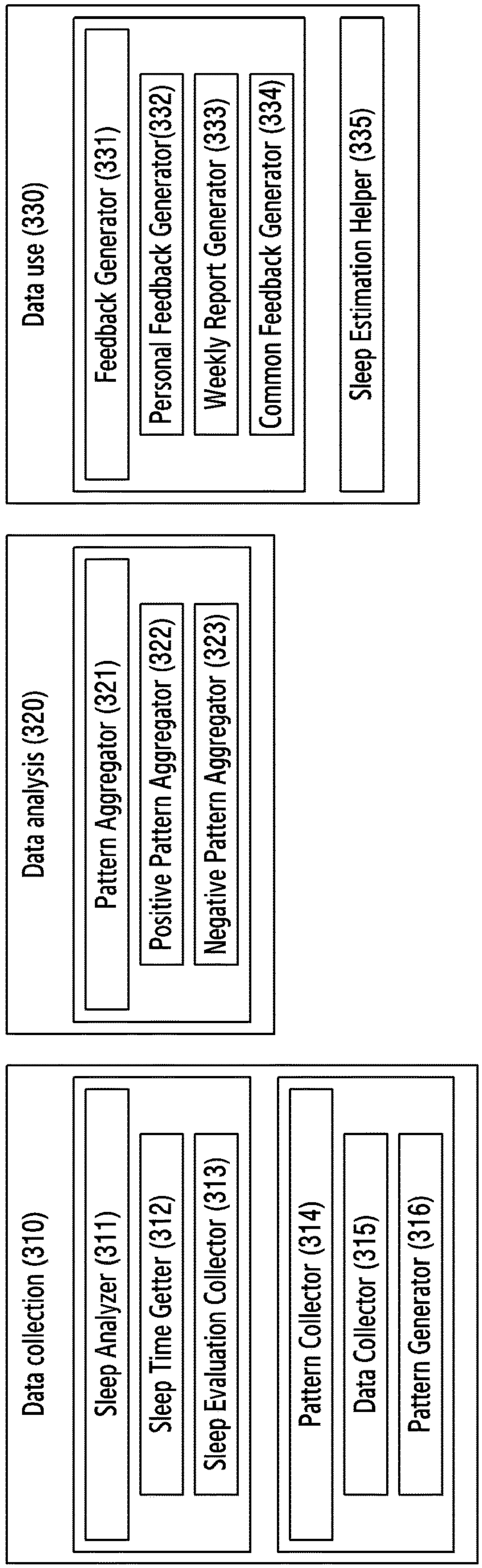
FIG. 3 illustrates detailed configuration modules of the electronic device 200 according to an embodiment.

FIG. 3 illustrates detailed configuration modules of the electronic device 200 according to an embodiment. Functions or operations described with reference to FIG. 3 may be understood as functions performed by at least one processor 220 of the electronic device 200 of FIG. 2. At least one processor 220 may execute instructions (for example, computer-executable instructions) stored in the memory 230 to implement software modules illustrated in FIG. 3 and control hardware (for example, the display 210, the sensor module 240, or the communication module 250 of FIG. 2) related to the functions.

Referring to FIG. 3, the electronic device 200 may include a data collection module 310, a data analysis module 320, and a data use module 330.

In an embodiment, the data collection module 310 is a configuration for collecting data required for analyzing the sleep state of the user and may include a sleep analyzer 311 and a pattern collector 314.

In an embodiment, the sleep analyzer 311 may include a sleep time getter 312 for collecting sleep time information of the user and a sleep evaluation collector 313 for collecting sleep evaluation information corresponding to the sleep time information. The sleep time getter 312 may identify a bedtime and a wake-up time of the user on the basis of at least one of a user input or a screen on/off record detected by the electronic device 200, biometric data of the user (for example, a heart rate (HR) or heart rate variability (HRV)) acquired by one or more sensors (for example, the sensor module 240 of FIG. 2) or an external electronic device (for example, a smart watch) and calculate a sleep time of the user by using the identified bedtime and wake-up time. For example, when it is identified that the bedtime of the user is 11:30 p.m. and the wake-up time is 7:00 a.m. the next day, the sleep time getter 312 may determine seven-and-a-half hours corresponding to an interval between the bedtime and the wake-up time as the sleep time of the corresponding user. The sleep evaluation collector 313 may acquire sleep evaluation information on the basis of one or more evaluation items. The evaluation items may include at least one of a sleep score calculated on the basis of a sleep state recorded during sleep, sleep satisfaction input by the user, sleep efficiency indicating a ratio of the actual sleep time to the total sleep time, and/or a sleep rating determined on the basis of the sleep time information. For example, the sleep evaluation collector 313 may continuously monitor motion data and biometric data while the user sleeps and calculate the score of the sleep quality in consideration of the sleep state such as a sleep time, a sleep cycle, a sleep level, and/or motion during sleep estimated according to the monitored data. The sleep evaluation collector 313 may receive an input of the sleep satisfaction from the user within a predetermined time after the sleep. The sleep satisfaction may be input in the form of a star rating or a number. The sleep evaluation collector 313 may calculate the sleep efficiency on the basis of the actual sleep time except for the time in which motion of the user exceeds a predetermined level in the total sleep time of the user. The sleep evaluation collector 313 may determine the sleep rating on the basis of at least one of a bedtime, a wake-up time, and/or waking hours during sleep.

In an embodiment, the pattern collector 314 is a module for collecting action information of the user and may include a data collector 315 and a pattern generator 316. The data collector 315 may collect data related to activities or environments which may influence the sleep of the user. For example, the data collector 315 may acquire the action information on the basis of at least one of a usage record of an application, a record related to motion of the user, and/or context data. The application usage record may include at least one of a type of an application executed by the electronic device 200, a log record, a package name, and/or a use time. The motion-related record is data measured using the sensor module 240 included in the electronic device 200 or an external electronic device (for example, a smart watch) and may include at least one of a recorded step count of the user, quantity of motion, heartbeat data, or whether the user takes a nap. The context data indicates data related to the action or environment of the user estimated through the electronic device 200 and may be acquired on the basis of at least one of a phone call log of the user, location information, and/or weather information. The pattern generator 316 may convert the collected action information into a pattern object in a predetermined format and manage the same. For example, the pattern generator 316 may convert the action information into a pattern object in a predetermined format including at least one item among an action type, an action name, a time difference between the action occurrence time point and the sleep time, an action start time, and/or an action end time.

In an embodiment, the data analysis module 320 is a configuration for analyzing a pattern of the action information collected according to the sleep of the user and may include a pattern aggregator 321. The pattern aggregator 321 is a module for classifying and collecting patterns of the action information on the basis of the sleep evaluation information and may include a positive pattern aggregator 322 and a negative pattern aggregator 323. The positive pattern aggregator 322 may collect pattern objects of a day on which the sleep evaluation information exceeds the predetermined reference and thus is determined as positive. The negative pattern aggregator 323 may collect pattern objects of a day on which the sleep evaluation information does not satisfy the predetermined reference and thus is determined as negative. For example, when it is determined that the sleep satisfaction in the sleep evaluation information collected according to the first sleep time information is higher than a third level which is a reference level, the pattern aggregator 321 may classify a pattern object of action information corresponding to the first sleep time information as a positive pattern. The positive pattern aggregator 322 may collect and manage pattern objects classified as the positive pattern. In another example, when it is determined that the sleep rating in the sleep evaluation information collected according to the second sleep time information is 'poor', the pattern aggregator 321 may classify a pattern object of action information corresponding to the second sleep time information as a negative pattern. The negative pattern aggregator 323 may collect and manage pattern objects classified as the negative pattern.

In an embodiment, the data use module 330 is a configuration for providing user-customized sleep guide information by using the pattern analysis result of action information and may include a feedback generator 331 and a sleep estimation helper 335.

In an embodiment, the feedback generator 331 is a module which generates personalized sleep guide information of the user and may include a personal feedback generator 332, a weekly report generator 333, and/or a common feedback generator 334. The personal feedback generator 332 may generate the sleep guide information on the basis of the collected positive patterns or negative patterns. For example, the personal feedback generator 332 may determine, as a good sleep habit, a pattern having the highest frequency among pattern objects of action information collected as the positive pattern, and generate feedback for maintaining the good sleep habit as the sleep guide information. For example, when it is assumed that an action pattern related to '30-minute exercise before sleep' is classified as the positive pattern, the personal feedback generator 332 may generate the content that helps for maintaining the habit of the '30-minute exercise before sleep' as the sleep guide information. In another example, the personal feedback generator 332 may determine, as a bad sleep habit, a pattern having the highest frequency among pattern objects of action information collected as the negative pattern and generate feedback for improving the bad sleep habit as the sleep guide information. When an action pattern related to 'the use of a video application before sleep' is classified as the negative pattern, the personal feedback generator 332 may generate the content that proposes improvement of the habit of 'the use of a video application before sleep' as the sleep guide information. The weekly report generator 333 may generate sleep statistics collected for one week and the pattern analysis result in the form of a weekly report. For example, the weekly report generator 333 may generate statistical analysis data of the sleep time information and the sleep evaluation information collected for one week as the weekly report. Further, the weekly report generator 333 may insert information indicating which part of the sleep evaluation increases or decreases through comparison with the weekly report of the previous week and indicating which sleep habit should be maintained or improved into the weekly report. For a user to which no personalized feedback can be provided due to the lack of data required for analyzing the sleep pattern, the common feedback generator 334 may generate the sleep guide information on the basis of a profile of the corresponding user. The profile may include at least one of gender, age, and/or residence of the user. For example, the common feedback generator 334 may download sleep statistics data of the same gender and age as the user from an external server and generate the content related to the generally good sleep habit as the sleep guide information on the basis of the downloaded data.

In an embodiment, the sleep estimation helper 335 may estimate the sleep time in consideration of the pattern analysis result of the action information. The sleep estimation helper 335 may increase the accuracy of estimation of the sleep time by additionally reflecting the pattern analysis result of the action information in the existing algorithm for estimating the sleep time on the basis of the user input or the screen on/off record.

Figure 4A:
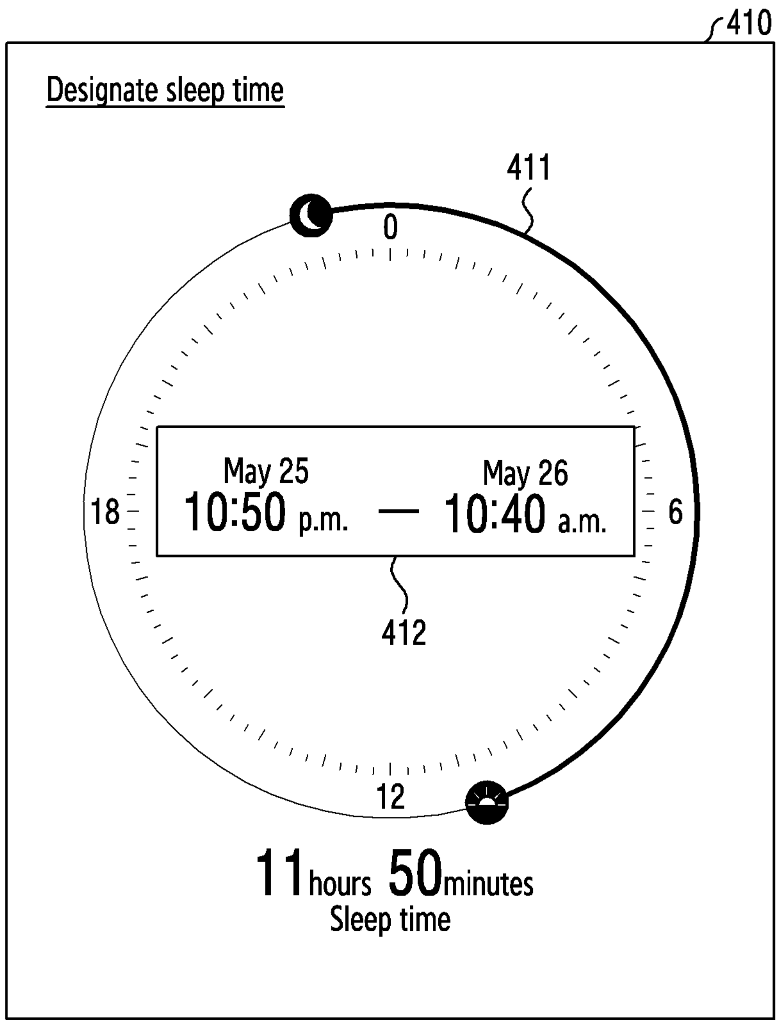
FIGS. 4A, 4B, and 4C illustrate the operation of acquiring sleep time information according to an embodiment.
Figure 4B:
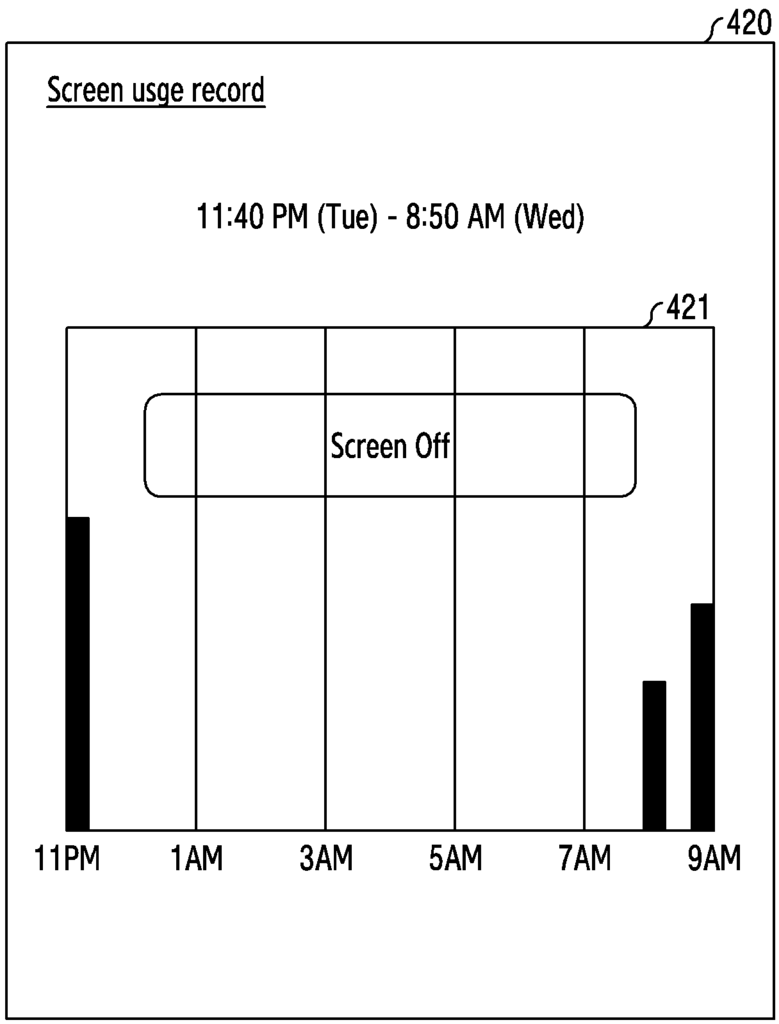
Figure 4C:
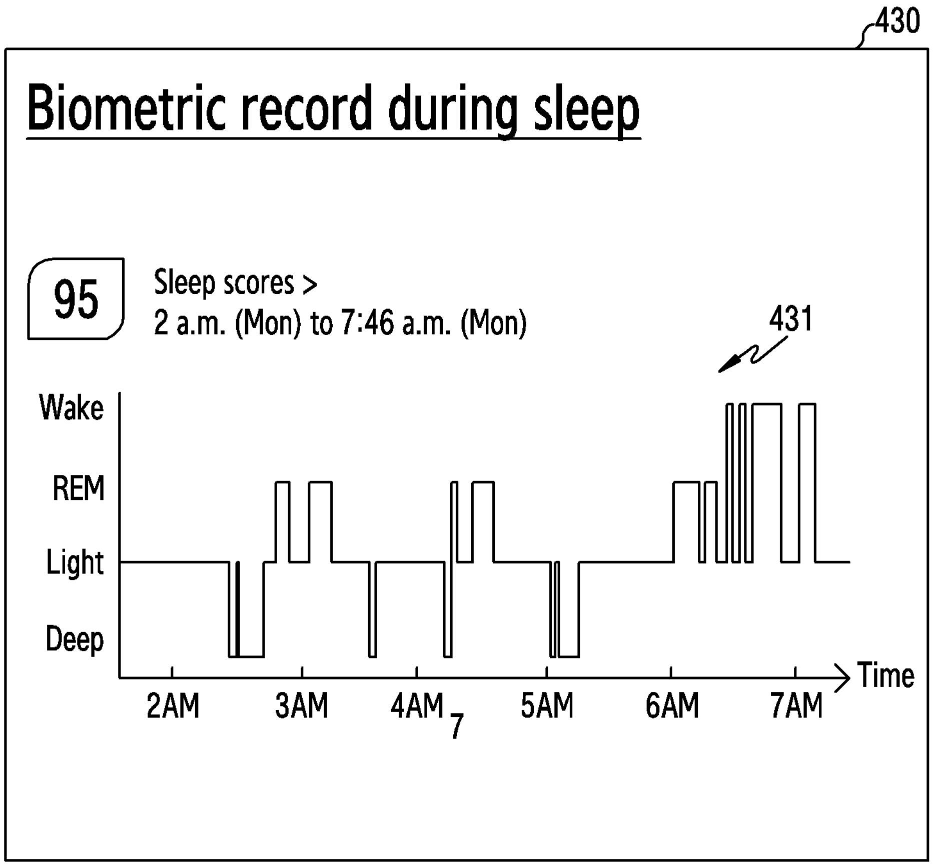

FIGS. 4A, 4B, and 4C illustrate the operation of acquiring sleep time information according to an embodiment. The electronic device 200 may acquire sleep time information of the corresponding user on the basis of a bedtime and a wake-up time estimated for the user. The bedtime/wake-up time may be estimated on the basis of at least one of the user input, the screen on/off record, and/or biometric data recorded for the user.

In FIG. 4A, the electronic device 200 may acquire the sleep time information on the basis of the bedtime and the wake-up time input by the user. According to an embodiment, the electronic device 200 may directly receive an input of the bedtime and the wake-up time from the user through a sleep time designation UI 410. For example, the user may input the bedtime and the wake-up time through a slide bar 411 in the shape of a clock provided within the sleep time designation UI 400. In another example, the user may input the bedtime and the wake-up time through a sleep time configuration bar 412 displayed within the sleep time designation UI 410. According to various embodiments, input time of the slide bar 411 and input time of the sleep time configuration bar 412 within the sleep time designation UI 410 may be synchronized. In response to movement of a moon icon or a sun icon of the slide bar 411 by the user, the electronic device 200 may change and display the bedtime and the wake-up time of the sleep time configuration bar 412. In response to an input of the bedtime and the wake-up time through the sleep time configuration bar 412 by the user, the electronic device 200 may move and display the location of the moon icon or the sun icon of the slide bar 411. The electronic device 200 may automatically calculate the sleep time on the basis of the bedtime and the wake-up time input through the sleep time designation UI 410 and acquire the calculated sleep time as the sleep time information.

In FIG. 4B, the electronic device 200 may acquire the sleep time information on the basis of a screen usage record 420 detected through the display. According to an embodiment, the electronic device 200 may identify the bedtime and the wake-up time from the screen usage record 420. For example, the electronic device 200 may identify that 11:40 p.m. at which a screen off interval starts is the bedtime and 8:50 a.m. at which the screen off interval ends is the wake-up time in a screen record by time 421. According to various embodiments, the electronic device 200 may estimate the sleep time in consideration of all of the sleep time identified on the basis of the user input and the sleep time identified on the basis of the screen record in order to increase the accuracy of the sleep time estimation. The electronic device 200 may determine that 11:40 p.m. corresponding to the later time among 10:50 p.m. which is the bedtime input by the user and 11:40 p.m. at which the screen off interval starts as the bedtime of the user. The electronic device 200 may determine 8:50 a.m. corresponding to the earlier time among 10:40 a.m. which is the wake-up time input by the user and 8:50 a.m. at which the screen off interval ends as the wake-up time of the user. The electronic device 200 may estimate, as the sleep time of the user, a time interval in which the sleep time identified on the basis of the user input overlaps the sleep time identified on the basis of the screen off interval. According to various embodiments, the electronic device 200 may estimate the sleep time additionally in consideration of motion information detected by the electronic device 200 as well as the user input and the screen record. The motion information may be acquired from one or more sensors (for example, the sensor module 176 of FIG. 1 or the sensor module 240 of FIG. 2). For example, when it is identified that motion is detected at 11:50 p.m. after the estimated bedtime (11:40 p.m.), the electronic device 200 may determine the bedtime of the user as 11:50 p.m. The electronic device 200 may additionally consider a biometric record during sleep as well as the motion information as illustrated in FIG. 4C.

In FIG. 4C, the electronic device 200 may acquire the sleep time information on the basis of the biometric record 430 during sleep collected for the user. According to an embodiment, the electronic device 200 may acquire biometric data measured by one or more sensors (for example, the sensor module 176 of FIG. 1 or the sensor module 240 of FIG. 2) or acquire the biometric data from an external electronic device (for example, a wearable device which the user is wearing). The biometric data may include a heart rate or heart rate variability. For example, the electronic device 200 may detect the bedtime and the end time (wake-up time) of the user on the basis of the biometric data and the motion data and analyze the sleep state of the user. The electronic device 200 may identify the total sleep time (for example, the total sleep time of the user for one night), data related to a sleep level (for example, hypnogram, and/or sleep time for each sleep level), and/or data related to at least one sleep cycle on the basis of analysis of the sleep state. For example, the sleep level may be classified into a first sleep level (awakening level) indicating awakening during sleep, a second sleep level indicating light non-REM sleep, a third sleep level indicating deep non-REM sleep, and/or a fourth sleep level (slow wave sleep level) indicating a fourth sleep level. The electronic device 200 may analyze a change in sleep levels corresponding to a change in the sleep state of the user during sleep and generate a sleep curve 431 corresponding to the analyzed change in sleep levels. The electronic device 200 may identify at least one sleep cycle for the sleep of the user on the basis of the sleep curve 431. Further, the electronic device 200 may identify the number of sleep cycles and/or time of each sleep cycle during the total sleep time on the basis of the at least one sleep cycle.

FIGS. 5A, 5B, 5C, and 5D illustrate the operation of acquiring sleep evaluation information according to an embodiment. The electronic device 200 may acquire sleep evaluation information corresponding to the sleep time information on the basis of one or more sleep evaluation items. The sleep evaluation items may include at least one of a sleep score calculated on the basis of the sleep state recorded during sleep, sleep satisfaction input by the user, sleep efficiency indicating a ratio of the actual sleep time to the total sleep time, and/or a sleep rating determined on the basis of the sleep time information.

Figure 5A:
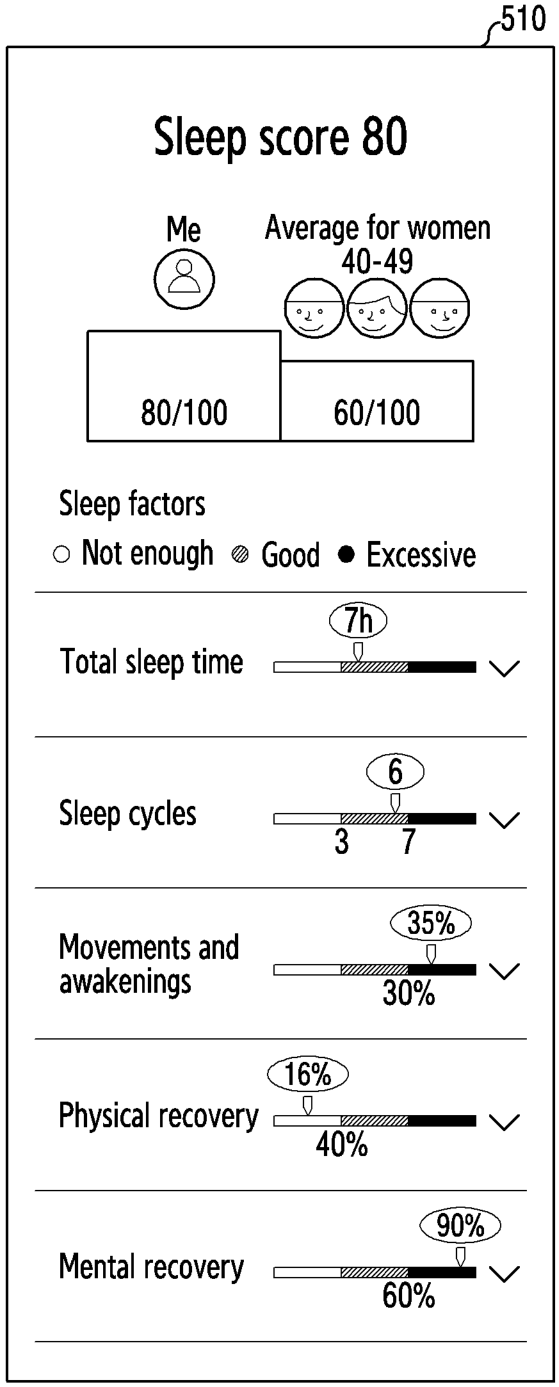
FIGS. 5A, 5B, 5C, and 5D illustrate the operation of acquiring sleep evaluation information according to an embodiment.

In FIG. 5A, the electronic device 200 may identify the sleep score 510 on the basis of analysis of the sleep state. According to an embodiment, the electronic device 200 may analyze one or more evaluation reference elements such as the total sleep time, the sleep cycle, the sleep level, and/or motion during sleep on the basis of biometric data and motion data of the user detected during sleep and calculate the sleep score corresponding to the analysis result. For example, the electronic device 200 may identify a change in the sleep level such as the awakening, light non-REM sleep, deep non-REM sleep, and/or REM sleep on the basis of the biometric data and the motion data and monitor the change or repetition of the sleep level to identify the sleep cycle. For each of the one or more evaluation reference elements, the electronic device 200 may identify an average value of a set corresponding to the profile of the user and determine the score for each evaluation reference element on the basis thereof. The electronic device 200 may determine the sleep score by summing the scores for respective evaluation reference elements. The sleep score may be determined within a range from 0 to 100.

Figure 5B:
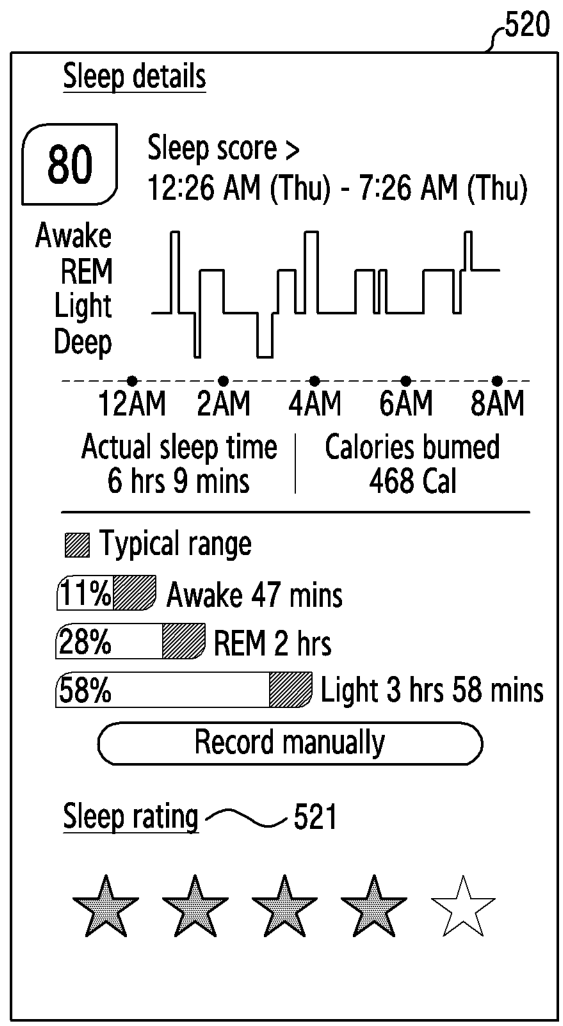

In FIG. 5B, the electronic device 200 may identify the sleep satisfaction on the basis of the user input. According to an embodiment, the electronic device 200 may directly receive an input of sleep satisfaction from the user through a sleep state display UI 520. The electronic device 200 may provide the analysis result for the sleep state on a predetermined day and induce the user to input sleep satisfaction in consideration of the analysis result. For example, the user may input its own sleep satisfaction through a rating bar 521 on the lower part of the sleep state display UI 520. According to various embodiments, the sleep satisfaction may be implemented to be input in the form of a star rating as well as in the form of a number from 1 to 5.

Figure 5C:
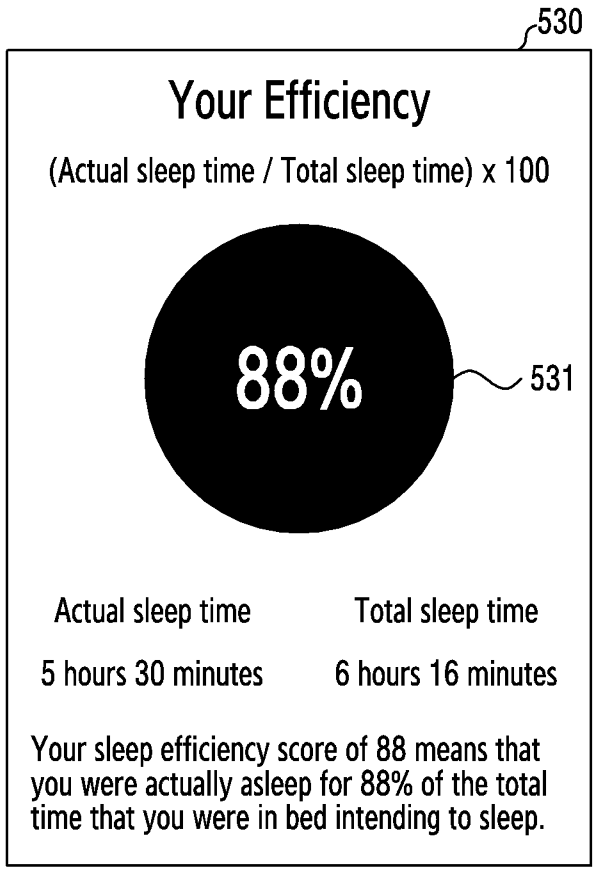

In FIG. 5C, the electronic device 200 may identify the total sleep time of the user and the sleep efficiency 530 by using motion data recorded while the user sleeps. The total sleep time may be identified on the basis of at least one of a bedtime/wake-up time input by the user, a screen on/off record, and/or biometric data recorded during sleep. According to an embodiment, the electronic device 200 may identify the actual sleep time except for the time in which motion of the user exceeds a predetermined level in the total sleep time and calculate a ratio of the actual sleep time to the total sleep time within a range from 0 to 100%. For example, when it is detected that the total sleep time is 6 hours and 16 minutes and there is motion exceeding a predetermined level for 46 minutes during the time, the electronic device 200 may identify 5 hours and 30 minutes except for 46 minutes from the total sleep time (6 hours and 16 minutes) as the actual sleep time. The electronic device 200 may determine 88% in a displayed object 531 which is a ratio of the actual sleep time to the total sleep time as the sleep efficiency.

Figure 5D:
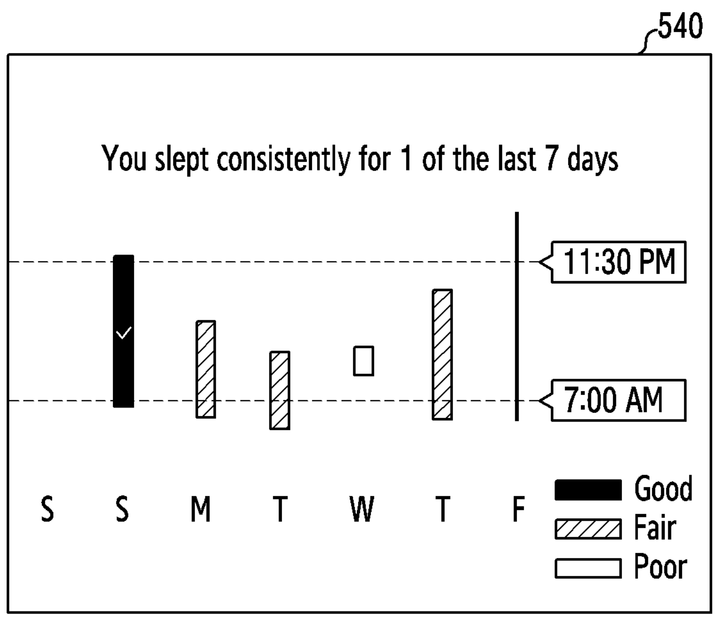

In FIG. 5D, the electronic device 200 may identify the sleep rating 540 in consideration of at least one of the bedtime of the user, the wake-up time, and/or waking hours during sleep. According to an embodiment, the electronic device 200 may compare the bedtime/wake-up time of the user with a reference configuration time and determine how much the user continuously maintains the sleep without waking during the sleep time, so as to determine the sleep rating. The reference configuration time may be determined on the basis of the bedtime/wake-up time input by the user or the average bedtime/wake-up time of the set corresponding to the profile of the user. The sleep rating may be divided into good, fair, or poor.

In an embodiment, the electronic device 200 may store sleep evaluation items collected as illustrated in FIGS. 5A to 5D in the memory (for example, the memory 130 of FIG. 1 or the memory 230 of FIG. 2) or a database which can be accessed by the electronic device 200. The electronic device 200 may determine the sleep evaluation information on the basis of the sleep evaluation items. For example, when it is identified that at least one of the sleep evaluation items satisfies a predetermined reference (for example, when the sleep score exceeds an average sleep score for each age, when sleep satisfaction is larger than or equal to a fourth level, when sleep efficiency is larger than or equal to 90%, and/or when the sleep rating is 'good'), the electronic device 200 may determine that the sleep evaluation information is positive or good. When it is identified that at least one of the sleep evaluation items does not satisfy the predetermined reference, the electronic device may determine the sleep evaluation information as negative or poor. When analysis results of the sleep evaluation items are at odds with each other, the electronic device 200 may determine the sleep evaluation information in consideration of a priority of each of the sleep evaluation items.

FIG. 6 illustrates a scheme in which action information 600 is collected and managed according to an embodiment. The electronic device 200 may acquire action information corresponding to the sleep time information on the basis of at least one of an application usage record, a record related to motion of the user detected by the sensor module (for example, the sensor module 176 of FIG. 1 or the sensor module 240 of FIG. 2) or an external electronic device (for example, a smart watch), and/or context data estimated on the basis of a network connection state of the electronic device 200. The application usage record may be identified on the basis of log data recorded in connection with an application executed in the electronic device 200 by the user, a type of the application, and/or a package name. The motion-related record may be identified on the basis of at least one of a recorded step count of the user, quantity of motion, heartbeat data, or whether the user takes a nap The context data indicates data related to the action or environment of the user estimated through the electronic device 200 and may be acquired on the basis of at least one of a phone call log, location information, or weather information of the user.

Referring to FIG. 6, the electronic device 200 may convert the action information into an object in a predetermined format and manage the same. The predetermined format may be an object in the structure including at least one item of an action type 601, an action name 603, an occurrence type 605, an occurrence gap 607, a start time 609, an end time 611, and/or a time offset 613.

The action type 601 indicates which type of the action corresponds to the action information and may be classified in connection with at least one of the application usage record, the motion-related record, and/or the context data. The electronic device 200 may store the action type 601 of the action information as object type data.

The action name 603 indicates a title of the action information and may include at least one of a package name of the executed application, a type of the motion-related record (for example, walking, running, cycling, stretching, nap, or other exercises), and/or a type of the context data (for example, going out, coming home, call, business, study, climbing, indoor exercise, outdoor exercise, listening to music, or other hobbies). The electronic device 200 may store the action name 603 of the action information as string type data.

The occurrence type 605 may indicate whether the action information is associated with the bedtime/wake-up time of the user or is generated during the sleep time. The electronic device 200 may store the occurrence type 605 of the action information as 4-byte integer type data.

The occurrence gap 607 may indicate a time difference between a time point at which an action of the action information occurs and the sleep time. The electronic device 200 may identify how much the action information influences sleep of the user on the basis of the occurrence gap 607 and may store the occurrence gap 607 of the action information as 8-byte integer (long) type data.

The start time 609 may indicate an action start time of the action information, and the end time 611 may indicate an action end time of the action information. The time offset 613 may indicate a time variation allowed for time data of the action information. The electronic device 200 may store the start time 609, the end time 611, and the time offset 613 as 8-byte integer (long) type data.

Figure 7:
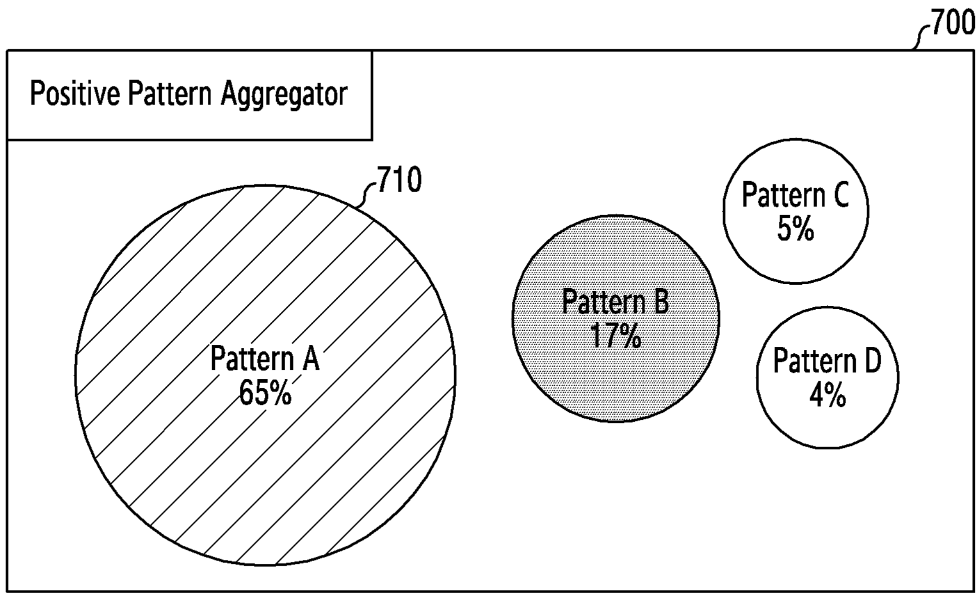
FIG. 7 illustrates a scheme of analyzing a pattern of action information according to an embodiment.

FIG. 7 illustrates a scheme of analyzing a pattern of action information according to an embodiment. In an embodiment, the electronic device 200 may classify action information into a positive pattern or a negative pattern on the basis of sleep evaluation information. For example, when it is identified that sleep evaluation information collected according to first sleep time information satisfies a predetermined reference (for example, when the sleep score exceeds an average sleep score for each age, when sleep satisfaction is larger than or equal to a fourth level, when sleep efficiency is larger than or equal to 90%, and/or when the sleep rating is 'good'), the electronic device 200 may determine that the sleep evaluation information is positive or good and classify a pattern of action information corresponding to the first sleep time information as a positive pattern. When it is identified that sleep evaluation information collected according to second sleep time information does not satisfy the predetermined reference, the electronic device 200 may determine that the sleep evaluation information is negative or poor and classify a pattern of action information corresponding to the second sleep time information as a negative pattern. The pattern analysis result of the action information may be used for generating sleep guide information for the user.

Referring to FIG. 7, the electronic device 200 may determine that a pattern A 710 having the highest frequency among one or more action patterns classified as a positive pattern set 700 is a main pattern and identify that the determined main pattern is a positive sleep habit of the user. The electronic device 200 may generate the sleep guide information to include the content that helps for continuously maintaining the identified positive sleep habit.

Similarly, the electronic device 200 may determine a main pattern generated with the statistically highest probability among one or more action patterns classified as a negative pattern set as a negative sleep habit of the user. The electronic device 200 may generate the sleep guide information to include the content that helps for improving the determined negative sleep habit.

Figure 8A:
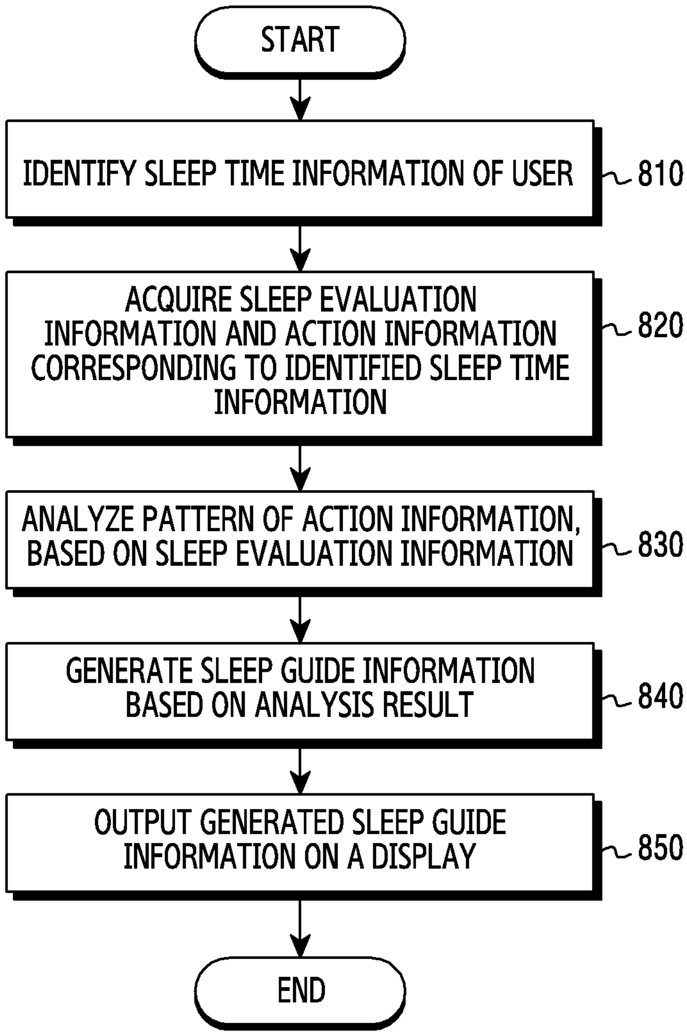
FIGS. 8A and 8B are flowcharts illustrating a method of operating an electronic device according to an embodiment.
Figure 8B:
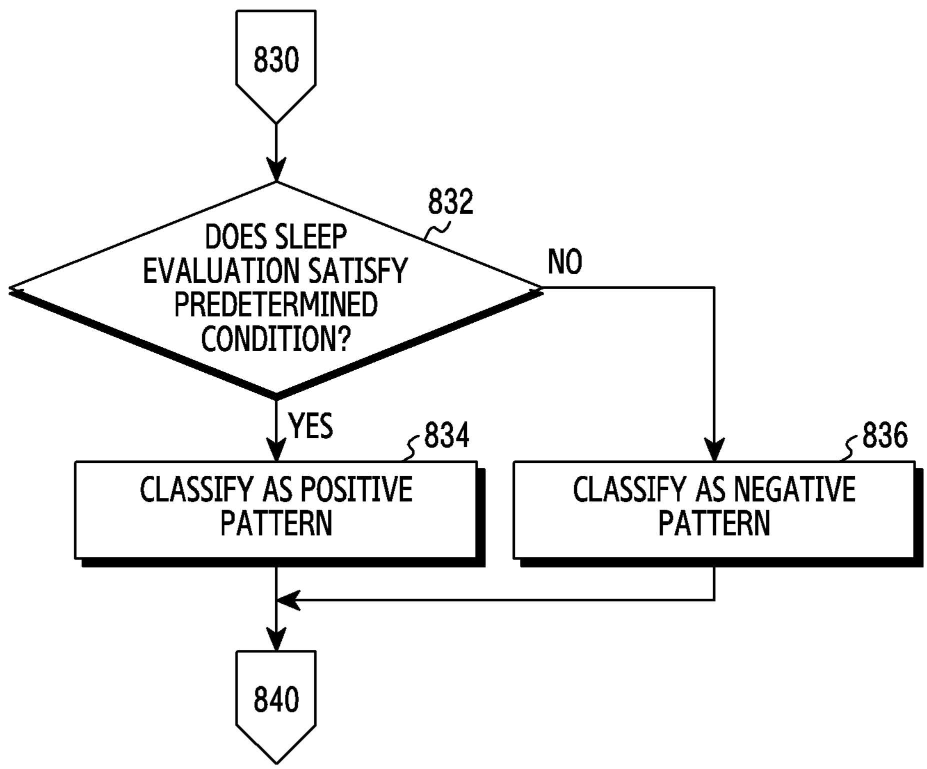

FIGS. 8A and 8B are flowcharts illustrating a method of operating an electronic device according to an embodiment. According to an embodiment, the electronic device 200 is a device which measures and analyzes sleep states of the user and guides the user to maintain a good sleep habit and improve a bad sleep habit and may correspond to the electronic device 101 of FIG. 1. Operations of FIGS. 8A and 8B may be performed by at least one processor (for example, the processor 120 of FIG. 1 or at least one processor 220 of FIG. 2) included in the electronic device 200.

Referring to FIG. 8A, in operation 810, the electronic device 200 may identify sleep time information of the user. The sleep time information is an index indicating how much the user sleeps for one day and may be calculated on the basis of a bedtime and a wake-up time of the user. In operation 810, the electronic device 200 may identify the sleep time information on the basis of at least one of a user input, a screen on/off record, and/or biometric data of the user. For example, the electronic device 200 may receive an input of the bedtime and the wake-up time from the user or estimate the bedtime and the wake-up time of the user on the basis of the screen on or screen off record detected by a display (for example, the display module 160 of FIG. 1 or the display 210 of FIG. 2). In another example, the electronic device 200 may estimate the bedtime and the wake-up time of the user on the basis of the biometric information of the user acquired from the sensor module (for example, the sensor module 176 of FIG. 1 or the sensor module 240 of FIG. 2) or an external electronic device (for example, a smart watch).

According to an embodiment, in operation 820, the electronic device 200 may acquire sleep evaluation information and action information corresponding to the sleep time information. For example, the electronic device 200 may acquire the sleep evaluation information on the basis of at least one evaluation item. The sleep evaluation information is an index which reflects evaluation for sleep of the user and may include at least one evaluation item among a sleep score calculated on the basis of a sleep state recorded during sleep, sleep satisfaction input by the user, sleep efficiency indicating a ratio of the actual sleep time to the total sleep time, and/or a sleep rating determined on the basis of the sleep time information. The sleep score is an item for objectively evaluating the sleep quality in consideration of one or more evaluation reference elements and may be obtained by scoring the sleep quality on the basis of the one or more evaluation reference elements determined by the American sleep foundation For example, the evaluation reference elements may reflect a sleep state such as sleep time, a sleep cycle, a sleep level, and/or motion during sleep. At least one processor 220 may analyze a change in sleep levels or a sleep cycle on the basis of biometric data (for example, heart rate (HR) or heart rate variability (HRV)) detected during the sleep time of the user and a degree of motion during sleep and calculate a sleep score corresponding to the analysis result. The sleep level may be divided into awakening, light non-REM sleep, deep non-REM sleep, and/or REM sleep, and the sleep cycle may be determined according to the change in the sleep levels. The sleep satisfaction is an item which reflects a user's subjective evaluation for the sleep and may be determined by a user input. The sleep efficiency is an item indicating the actual sleep time except for the time in which a user's motion exceeds a predetermined level in the total sleep time and may be determined within a range from 0% to 100%. The sleep rating may be an item evaluated on the basis of at least one of a bedtime of the user, a wake-up time, and/or waking hours during sleep.

In operation 820, the electronic device 200 may acquire action information corresponding to the sleep time information in consideration of motion of the user collected through the electronic device 200 or context data. The action information is an index indicating a user's action that may influence sleep and may include at least one of a usage record of an application executed by the electronic device 200, a record related to a user's motion detected by the sensor module 240 or an external electronic device (for example, a smart watch), and/or context data estimated on the basis of a network connection state of the electronic device 200. The application usage record may be acquired on the basis of log data recorded in connection with the application executed by the user, and the motion-related record may be acquired on the basis of at least one of a recorded step count of the user, quantity of motion, heartbeat data, and/or whether the user takes a nap. The context data indicates data related to the action or environment of the user estimated through the electronic device 200 and may be acquired on the basis of at least one of a phone call log, location information, or weather information of the user. According to various embodiments, the action information may be stored and managed in a predetermined format to analyze a sleep habit of the user. The electronic device 200 may convert the action information into a first format including at least one of an action type, an action name, a time difference between an action occurrence time point and sleep time, an action start time, and/or an action end time and manage the action information converted into the first format in the memory 230 or a database which can be accessed by the electronic device 200. For example, when acquiring action information indicating that the user uses a game application for one hour before going to bed, the electronic device 200 may convert the acquired action information according to the first format and manage the same.

According to an embodiment, in operation 830, the electronic device 200 may analyze a pattern of the action information on the basis of the sleep evaluation information. A detailed description of the pattern analysis in operation 830 is made with reference to FIG. 8B.

Referring to FIG. 8B, in operation 832, the electronic device 200 may determine whether sleep evaluation information acquired according to the sleep time information satisfies a predetermined reference. The predetermined reference may be determined on the basis of the at least one evaluation item included in the sleep evaluation information. For example, the case in which the sleep score exceeds an average sleep score for each age, the case in which sleep satisfaction is larger than or equal to a fourth level, the case in which sleep efficiency is larger than or equal to 90%, or the case in which the sleep rating is 'good' may be configured as the predetermined reference for each sleep evaluation item.

When it is identified that the sleep evaluation information satisfies the predetermined reference on the basis of the determination result (operation 832-Yes), the electronic device 200 may classify action information acquired according to the sleep time information as a positive pattern in operation 834. For example, when it is identified that the sleep score corresponding to the first sleep time information is larger than an average sleep score of the user's age, the electronic device 200 may classify action information collected according to the first sleep time information as a positive pattern.

When it is identified that the sleep evaluation information does not satisfy the predetermined reference on the basis of the determination result (operation 832-No), the electronic device 200 may classify the action information acquired according to the sleep time information as a negative pattern in operation 836. For example, when it is identified that the sleep efficiency corresponding to the second sleep time information is lower than the predetermined reference (for example, 80%), the electronic device 200 may classify action information collected according to the second sleep time information as a negative pattern.

According to an embodiment, the electronic device 200 may determine a sleep habit of the user on the basis of the pattern classification result of the action information. For example, the electronic device 200 may determine that a positive pattern having the highest frequency among one or more action patterns classified as the positive pattern is a first sleep habit of the user. The electronic device 200 may determine that a negative pattern having the highest frequency among one or more action patterns classified as the negative pattern is a second sleep habit of the user.

Referring back to FIG. 8A, in operation 840, the electronic device 200 may generate sleep guide information of the user on the basis of the analysis result. In operation 840, the electronic device 200 may generate the sleep guide information on the basis of at least one of the first sleep habit or the second sleep habit. For example, the electronic device 200 may generate the sleep guide information to include the content that helps for continuously maintaining the first sleep habit or the content that helps for improving the second sleep habit. According to various embodiments, the electronic device 200 may also generate the sleep guide information in consideration of a profile of the user. The profile may include at least one of gender, age, and/or residence of the user. When the user is a male in his 30s, at least one processor 220 may generate sleep statistics for men in their 30s and a comment for improving the sleep quality as the sleep guide information.

According to an embodiment, in operation 850, the electronic device 200 may output the generated sleep guide information to a display (for example, the display module 160 of FIG. 1 or the display 210 of FIG. 2). When a predetermined condition (for example, time or location) is satisfied, the electronic device 200 may output the sleep guide information. The output condition of the sleep guide information may be configured by the user and may additionally use output means (for example, the sound output module 155 and the haptic module 179 of FIG. 1) included in the electronic device 200 as well as the display.

Figure 9A:
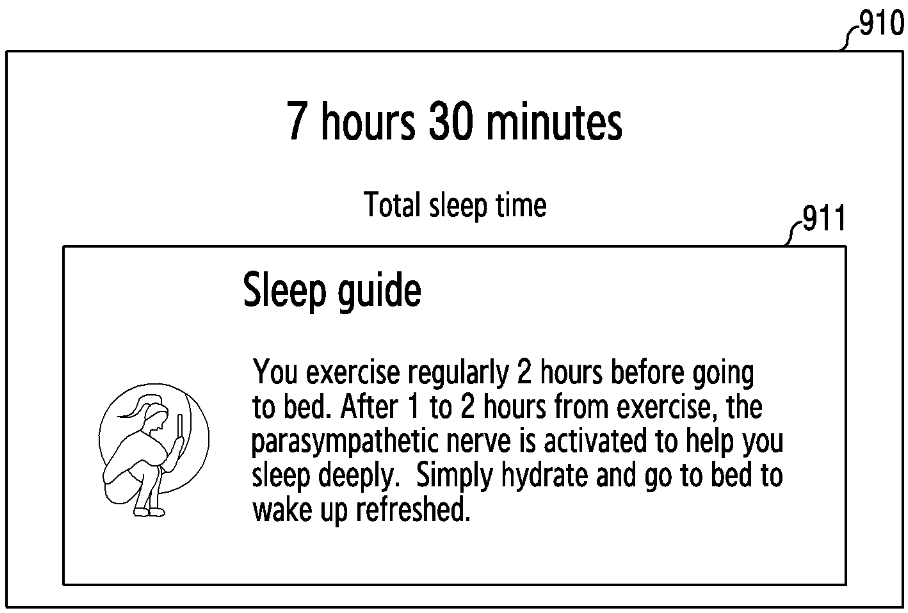
FIGS. 9A and 9B illustrate a scheme of providing personalized sleep guide information based on a user's action pattern according to an embodiment.
Figure 9B:
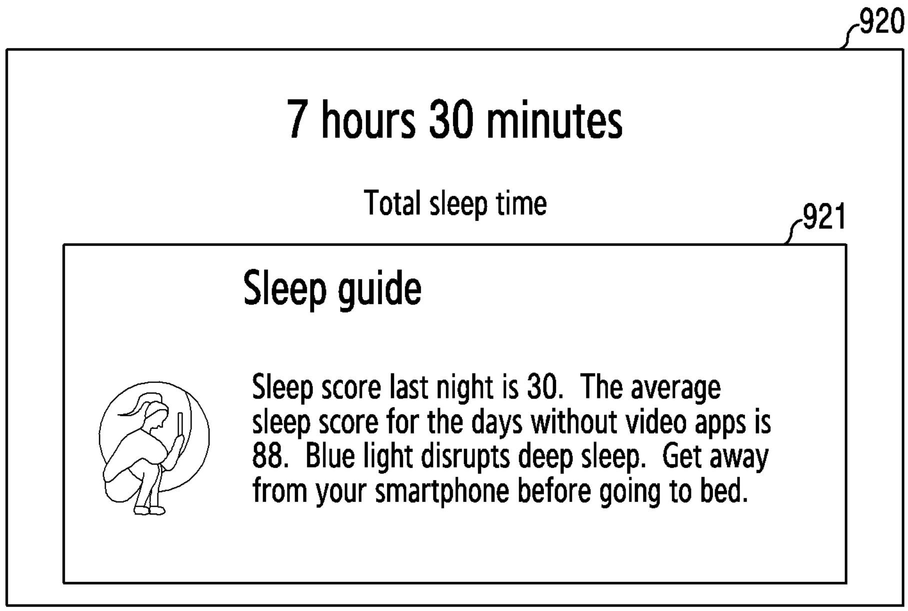

FIGS. 9A and 9B illustrate a scheme of providing personalized sleep guide information based on a user's action pattern according to an embodiment. In an embodiment, the electronic device 200 may generate and provide the sleep guide information on the basis of a sleep habit identified through analysis of the user's action information pattern.

Referring to FIG. 9A, the electronic device 200 may output a sleep guide message 910 generated on the basis of a positive sleep habit to a display (for example, the display 160 of FIG. 1 or the display 210 of FIG. 2). For example, when it is identified that the occurrence frequency of an action pattern of 'exercise two hours before bedtime' is high in action information classified for the user as a positive pattern, the electronic device 200 may determine that the action pattern of the 'exercise two hours before bedtime' is a positive sleep habit. The electronic device 200 may generate the sleep guide message 910 including a comment 911 that helps for maintaining the determined positive sleep habit and output the sleep guide message 910 to the display at a time configured by the user.

Referring to FIG. 9B, the electronic device 200 may output a sleep guide message 920 generated on the basis of a negative sleep habit to the display. For example, when it is identified that the occurrence frequency of an action pattern of 'the use of a video app late at night' in action information classified for the user as a negative pattern, the electronic device 200 may determine that the action pattern of 'the use of the video app late at night' as a negative sleep habit. The electronic device 200 may generate the sleep guide message 920 including a comment 921 that helps for improving the determined negative sleep habit and output the message at the configured time.

Figure 10A:
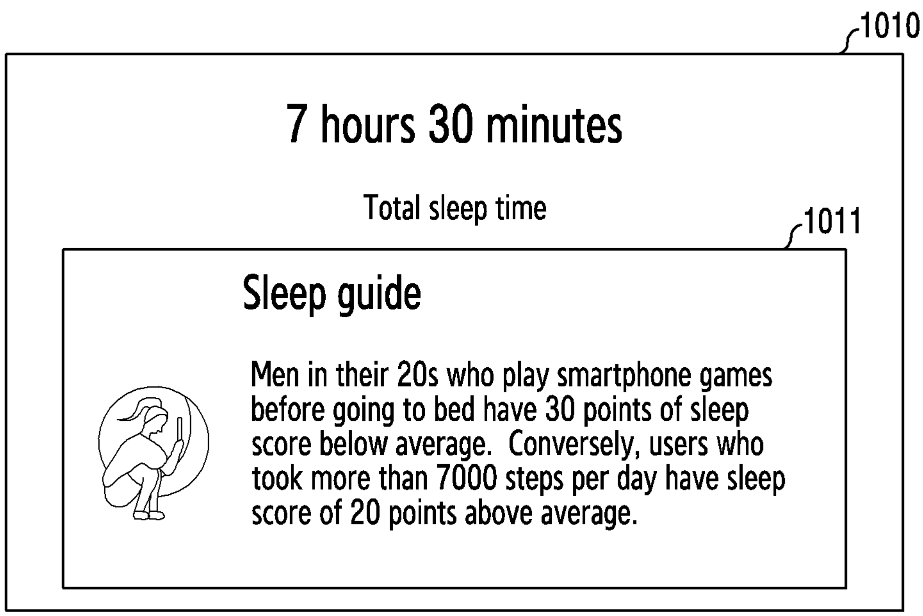
FIGS. 10A and 10B illustrate a scheme of providing personalized sleep guide information based on a profile of the user according to an embodiment.
Figure 10B:
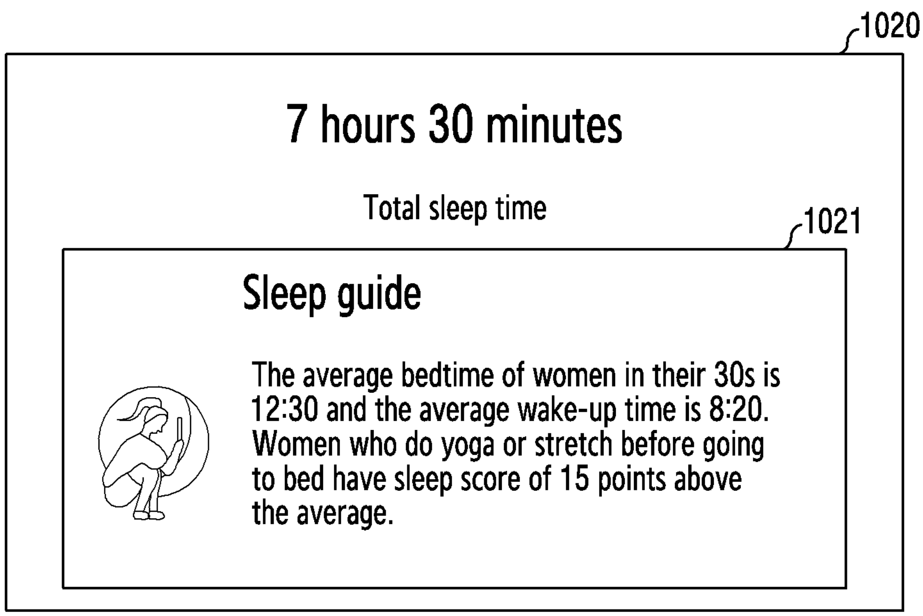

FIGS. 10A and 10B illustrate a scheme of providing personalized sleep guide information based on a profile of the user according to an embodiment. In an embodiment, for a user to which personalized feedback cannot be provided due to the lack of data required for analyzing the sleep pattern, the electronic device 200 may generate and provide the sleep guide information on the basis of a profile of the corresponding user. The profile may include at least one of gender, age, or residence of the corresponding user.

Referring to FIG. 10A, the electronic device 200 may identify that the user's profile is a male in his twenties (20s) and acquire data on an average sleep score of men in their 20s from an external server (for example, the server 108 of FIG. 1). The electronic device 200 may generate a sleep guide message 1010 including a comment 1011 that helps for improving a sleep habit on the basis of the acquired data and output the sleep guide message 1010 at a time configured by the user.

Referring to FIG. 10B, the electronic device 200 may identify that a user's profile is a female in her 30s and acquire data on an average bedtime and an average wake-up time of women in their 30s from an external server (for example, the server 108 of FIG. 1). The electronic device 200 may generate a sleep guide message 1020 including a comment 1021 about a sleep habit for improving the sleep quality on the basis of the acquired data and output the message at the configured time.

Figure 11A:
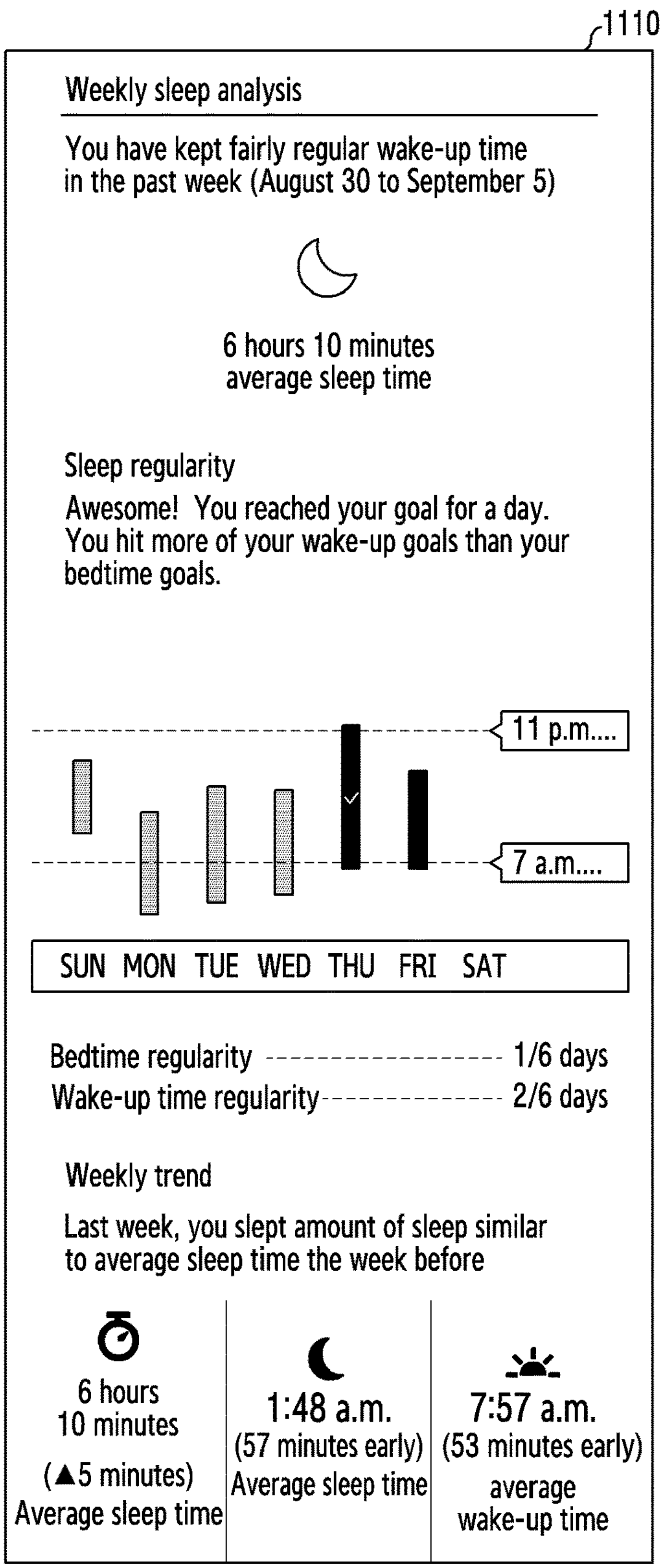
FIGS. 11A and 11B illustrate a scheme of generating and providing the result of analysis of an action pattern of the user according to an embodiment.
Figure 11B:
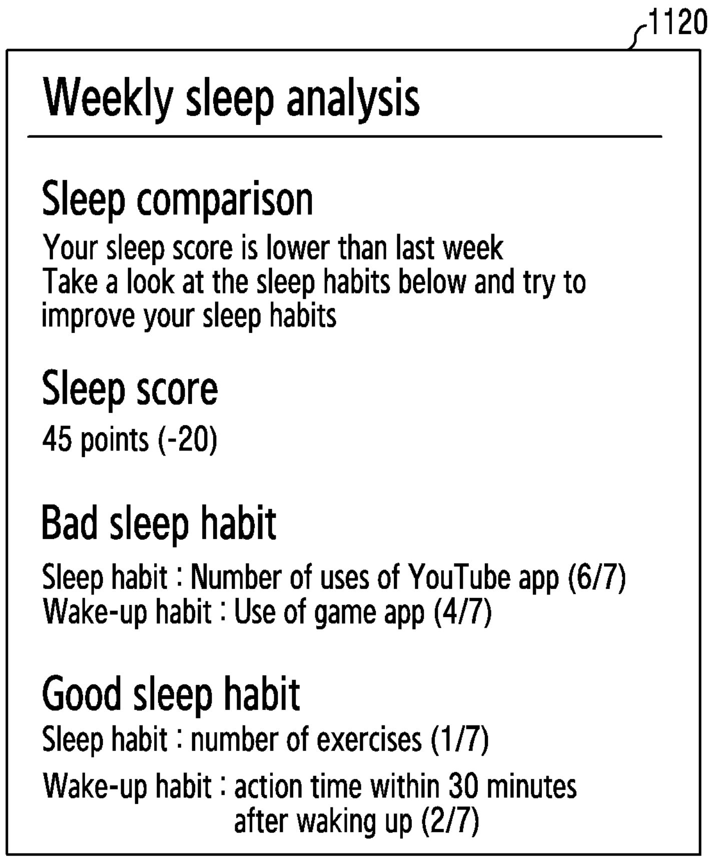

FIGS. 11A and 11B illustrate a scheme of generating and providing the result of analysis of an action pattern of the user according to an embodiment. In an embodiment, the electronic device 200 may generate and provide sleep statistics and the pattern analysis result, collected for one week, in the form of a weekly report.

Referring to FIG. 11A, the electronic device 200 may generate a weekly sleep analysis report 1110 on the basis of sleep time information and sleep evaluation information collected for one week. For example, the electronic device 200 may provide the analysis result for the average sleep time for one week, the sleep rating recorded for each day of week, and regularity of the bedtime/wake-up time as the weekly sleep analysis report 1110. Further, the electronic device 200 may additionally provide the result of comparison with sleep statistics of the previous week as the weekly sleep analysis report 1110.

According to an embodiment, the electronic device 200 may generate a weekly sleep analysis report 1120 on the basis of an action information pattern analyzed for one week in FIG. 11B. Referring to FIG. 11B, the electronic device 200 may provide statistics for a good sleep habit or a bad sleep habit made for one week and a comment about a sleep habit that should be maintained/improved as the weekly sleep analysis report 1120.

An electronic device (for example, the electronic device 200) according to an embodiment may include a display (for example, the display 210), at least one processor (for example, the processor 220) operatively connected to the display, and a memory (for example, the memory 230) operatively connected to the at least one processor, and the memory may be configured to store instructions causing the at least one processor to, when executed, identify sleep time information of a user, acquire sleep evaluation information and action information corresponding to the sleep time information, analyze a pattern of the action information, based on the sleep evaluation information, generate sleep guide information for the user, based on a result of the analysis, and output the generated sleep guide information to the display.

In an embodiment, the instructions may cause the at least one processor to identify the sleep time information, based on at least one of a user input, a screen on or screen off record detected by the display, and/or biometric data of the user acquired from an external electronic device.

In an embodiment, the instructions may cause the at least one processor to acquire the sleep evaluation information, based on at least one item among a sleep score calculated based on a sleep state recorded during sleep, sleep satisfaction input by the user, sleep efficiency indicating a ratio of an actual sleep time to a total sleep time, and/or a sleep rating determined based on the sleep time information.

In an embodiment, the instructions may cause the at least one processor to acquire the action information, based on at least one of a usage record of an application executed by the electronic device, a motion-related record detected using at least one sensor (for example, the sensor module 240), and context data estimated based on a network connection state of the electronic device.

In an embodiment, the action information may be converted into a first format including at least one of an action type, an action name, a time difference between an action occurrence time point and a sleep time, an action start time, and/or an action end time and stored in the memory.

In an embodiment, the instructions may cause the at least one processor to classify the action information into a positive pattern or a negative pattern, based on the sleep evaluation information and store a result of the classification in the memory or a database which can be accessed by the electronic device.

In an embodiment, the instructions may cause the at least one processor to determine that a pattern having a highest frequency among one or more positive patterns stored in the memory or the database is a first sleep habit of the user and determine that a pattern having a highest frequency among one or more negative patterns stored in the memory or the database is a second sleep habit of the user.

In an embodiment, the instructions may cause the at least one processor to generate the sleep guide information, based on at least one of the first sleep habit or the second sleep habit.

In an embodiment, the instructions may cause the at least one processor to generate the sleep guide information, based on a user profile including at least one of gender, age, or residence of the user.

In an embodiment, the instructions may cause the at least one processor to output the generated sleep guide information to the display at a predetermined time point.

A method of operating an electronic device (for example, the electronic device 200) according to another embodiment may include an operation of identifying sleep time information of a user, an operation of acquiring sleep evaluation information and action information corresponding to the sleep time information, an operation of analyzing a pattern of the action information, based on the sleep evaluation information, an operation of generating sleep guide information for the user, based on a result of the analysis, and an operation of outputting the generated sleep guide information to the display.

In an embodiment, the operation of identifying the sleep time information of the user may include an operation of estimating the sleep time information, based on at least one of a user input, a screen on or screen off record detected by a display (for example, the display 210), and/or biometric data of the user acquired from an external electronic device (for example, the electronic device 102 or the electronic device 104).

In an embodiment, the operation of acquiring the sleep evaluation information and the action information corresponding to the sleep time information may include an operation of acquiring the sleep evaluation information, based on at least one item among a sleep score calculated based on a sleep state recorded during sleep, sleep satisfaction input by the user, sleep efficiency indicating a ratio of an actual sleep time to a total sleep time, and/or a sleep rating determined based on the sleep time information.

In an embodiment, the operation of acquiring the sleep evaluation information and the action information corresponding to the sleep time information may include an operation of acquiring the action information, based on at least one of a usage record of an application executed by the electronic device, a motion-related record detected using at least one sensor (for example, the sensor module 240), and context data estimated based on a network connection state of the electronic device.

In an embodiment, the method may further include an operation of converting the action information into a first format including at least one of an action type, an action name, a time difference between an action occurrence time point and a sleep time, an action start time, and/or an action end time and storing the action information in a memory (for example, the memory 230).

In an embodiment, the operation of analyzing the pattern of the action information, based on the sleep evaluation information may include an operation of classifying the action information into a positive pattern or a negative pattern, based on the sleep evaluation information and an operation of storing a result of the classification in the memory or a database which can be accessed by the electronic device.

In an embodiment, the operation of analyzing the pattern of the action information, based on the sleep evaluation information may include an operation of determining that a pattern having a highest frequency among one or more positive patterns stored in the memory or the database is a first sleep habit of the user and determining that a pattern having a highest frequency among one or more negative patterns stored in the memory or the database is a second sleep habit of the user.

In an embodiment, the method may further include an operation of generating the sleep guide information, based on at least one of the first sleep habit or the second sleep habit.

In an embodiment, the operation of generating the sleep guide information of the user may include an operation of generating the sleep guide information, based on a user profile including at least one of gender, age, and/or residence of the user.

In an embodiment, the operation of outputting the generated sleep guide information may include an operation of outputting the generated sleep guide information through the display or a speaker (for example, the sound output module 155) at a predetermined time point.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used in connection with various embodiments of the disclosure, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

The invention claimed is:

1. An electronic device comprising:

a display;

at least one processor; and memory storing instructions that, when executed by the at least one processor processor individually or collectively, cause the electronic device to:

identify sleep time information of a user;

acquire sleep evaluation information and action information corresponding to the sleep time information;

classify a positive pattern or a negative pattern of the action information, based on the sleep evaluation information;

determine that a first pattern having a highest frequency among action patterns classified by the positive pattern is a first sleep habit of the user;

determine that a second pattern having a highest frequency among action patterns classified by the negative pattern is a second sleep habit of the user;

generate sleep guide information for the user, based on at least one of the first sleep habit or the second sleep habit; and output, through the display, the generated sleep guide information.

2. The electronic device of claim 1, wherein the instructions, when executed by the at least one processor, cause the electronic device to identify the sleep time information, based on at least one of a user input, a screen on or screen off record detected by the display, or biometric data of the user acquired from an external electronic device.

3. The electronic device of claim 1, wherein the instructions, when executed by the at least one processor, cause the electronic device to acquire the sleep evaluation information, based on at least one item among a sleep score calculated based on a sleep state recorded during sleep, sleep satisfaction input by the user, sleep efficiency indicating a ratio of an actual sleep time to a total sleep time, or a sleep rating determined based on the sleep time information.

4. The electronic device of claim 1, wherein the instructions, when executed by the at least one processor, cause the electronic device to acquire the action information, based on at least one of a usage record of an application executed by the electronic device, a motion-related record detected using at least one sensor, and context data estimated based on a network connection state of the electronic device, and wherein the action information is converted into a first format comprising at least one of an action type, an action name, a time difference between an action occurrence time point and a sleep time, an action start time, or an action end time and stored in the memory.

5. The electronic device of claim 1, wherein the instructions, when executed by the at least one processor, cause the electronic device to store a classification result of the classifying in the memory or a database that is accessible by the electronic device.

6. The electronic device of claim 1, wherein the instructions, when executed by the at least one processor, cause the electronic device to generate the sleep guide information, based on a user profile comprising at least one of gender, age, or residence of the user.

7. The electronic device of claim 1, wherein the instructions, when executed by the at least one processor, cause the electronic device to output the generated sleep guide information at a predetermined time point.

8. A method comprising:

identifying sleep time information of a user;

acquiring sleep evaluation information and action information corresponding to the sleep time information;

classifying a positive pattern or a negative pattern of the action information, based on the sleep evaluation information;

determining that a first pattern having a highest frequency among action patterns classified by the positive pattern is a first sleep habit of the user;

determining that a second pattern having a highest frequency among action patterns classified by the negative pattern is a second sleep habit of the user;

generating sleep guide information for the user, based on at least one of the first sleep habit or the second sleep habit; and outputting the generated sleep guide information.

9. The method of claim 8, wherein the identifying of the sleep time information of the user comprises estimating the sleep time information, based on at least one of a user input, a screen on or screen off record detected by a display, or biometric data of the user acquired from an external electronic device.

10. The method of claim 8, wherein the acquiring of the sleep evaluation information and the action information corresponding to the sleep time information comprises acquiring the sleep evaluation information, based on at least one item among a sleep score calculated based on a sleep state recorded during sleep, sleep satisfaction input by the user, sleep efficiency indicating a ratio of an actual sleep time to a total sleep time, or a sleep rating determined based on the sleep time information.

11. The method of claim 8, wherein the acquiring of the sleep evaluation information and the action information corresponding to the sleep time information comprises:

acquiring the action information, based on at least one of a usage record of an application executed by an electronic device, a motion-related record detected using at least one sensor, and context data estimated based on a network connection state of the electronic device; and converting the action information into a first format comprising at least one of an action type, an action name, a time difference between an action occurrence time point and a sleep time, an action start time, or an action end time and storing the action information in a memory.

12. The method of claim 8, further comprising:

storing a classification result of the classifying in a memory or a database which is accessible by an electronic device.

13. The method of claim 8, wherein the generating of the sleep guide information of the user comprises generating the sleep guide information, based on a user profile comprising at least one of gender, age, or residence of the user.

* * * * *